US00PP10785P

United States Patent [19]

Poulsen

[11] Patent Number: Plant 10,785

[45] Date of Patent: Feb. 9, 1999

[54] ELATIOR BEGONIA PLANT NAMED 'BETTY'

[75] Inventor: Jens Nørgaard Poulsen, Aarhus N., Denmark

[73] Assignee: D. S. Cole Growers Inc., Loudon, N.H.

[21] Appl. No.: 853,961

[22] Filed: May 9, 1997

[51] Int. Cl.[6] ..... A01H 5/00

[52] U.S. Cl. ..... Plt./87.18

[58] Field of Search ..... Plt./87.18

[56] References Cited

PUBLICATIONS

GTITM UPOV–ROM citation for Begonia, L., 'Betty' JP PBR 8791, Aug. 1996.

*Primary Examiner*—Howard J. Locker
*Attorney, Agent, or Firm*—C. A. Whealy

[57] ABSTRACT

A distinctive cultivar of Elatior Begonia plant named Betty, characterized by its numerous fully double orange flowers; upright, spreading and vigorous growth habit; freely branching; good stem and stem base strength; dark green foliage; strong and vigorous root system that develops rapidly; resistance to Powdery Mildew under greenhouse conditions; and excellent postproduction longevity.

1 Drawing Sheet

The present invention relates to a new and distinctive cultivar of Begonia plant, biotanically known as *Begonia× hiemalis*, commercially known as Elatior Begonia, and hereinafter referred to by the cultivar name Betty.

The new cultivar was discovered by the inventor in Aarhus, Denmark, as a mutation of the Elatior Begonia cultivar Sanne (disclosed in U.S. Plant Pat. No. 9,430), and was observed in a group on 15-cm flowering plants of the parent cultivar in December, 1993.

Asexual reproduction of the new cultivar by terminal cuttings in Aarhus, Denmark, has shown that the unique features of this new Elatior Begonia are stable and are reproduced true to type in successive propagations.

The new cultivar has not been observed under all possible environmental conditions. The phenotype may vary significantly with variations in environment such as temperature, light level and daylength, without, however, any variance in genotype.

The following traits have been repeatedly observed and are determined to be the unique characteristics of Betty:

1. Numerous fully double orange flowers.
2. Upright, spreading and vigorous growth habit.
3. Freely branching.
4. Good stem and stem base strength.
5. Dark green foliage.
6. Strong and vigorous root system that develops rapidly.
7. Resistant to Powdery Mildew under greenhouse conditions.
8. Excellent postproduction longevity with plants maintaining good condition for about 6 weeks under interior conditions.

The following characteristics differentiate the new cultivar from the parent cultivar Saane and other Elatior Begonias commercially know and used in the floriculture industry, namely the cultivar Britta (disclosed in U.S. Plant Pat. No. 9,432):

1. Plants of the new cultivar are more vigorous than plants of the cultivars Britta and Sanne.
2. Plants of the new cultivar are taller than plants of the cultivar Britta.
3. Plants of the new cultivar have longer petioles and longer peduncles than plants of the cultivar Britta.
4. Flower color of the new cultivar is orange whereas flower color of plants of the cultivar Sanne is dark pink.
5. Flower color of plants of the new cultivar is darker and fades less than flower color of the cultivar Britta.

6. Petals of plants of the new cultivar are flatter than petals of plants of the cultivar Britta.
7. Plants of the new cultivar have stronger stem base than plants of the cultivars Britta and Sanne.

The accompany colored photograph illustrates the overall appearance and flower color of the new cultivar, showing the colors as true as it is reasonably possible to obtain in colored reproductions of this type.

The photograph comprises a side perspective view of a typical potted plant of Betty. Actual flower and foliage colors may differ from flower and foliage colors in the photograph due to light reflectance.

The following observations, measurements, values, and comparisons describe plants grown in Loudon, N.H., during the winter under commercial practice in a glass-covered greenhouse. In the following description, color references are made to The Royal Horticultural Society Colour Chart except where general terms of ordinary dictionary significance are used.

Botanical classification: *Begonia×hiemalis* cultivar Betty.

Commercial classification: Elatior begonia.

Parentage: Naturally-occuring mutation of *Begonia× hiemalis* cultivar Sanne.

Propagation:

*Type.*—By terminal cuttings.

*Time to initiate roots.*—Terminal cuttings root in 17 to 21 days at temperatures of 21C.

*Rooting habit.*—Root system is very strong, vigorous and develops rapidly. Roots are prolific and dense. Root texture is fine and fibrous.

Plant description:

*Plant form.*—Upright and spreading potted plant, freely branching with usually 5 branches per plant. Good stem and stem base strength. Flowers are fully double and abundant. Plants flower continuously under warm night temperatures.

*Growth habit.*—Vigorous. Suitable for 10-cm and larger containers. Under optimal environmental conditions, 10 to 12 weeks are required to produced proportional 10-cm potted plants and about 16 weeks are required to produce proportional 15-cm potted plants from terminal cutting that are directly-stuck in the container. Vegetative shoots are formed at basal nodes and flowering shoots are formed at upper nodes.

*Plant height.*—About 25 cm in a 15-cm pot.

*Plant width.*—About 25 cm in a 15-cm pot.

*Stem description.*—Lateral branch length: About 17 cm. Lateral branch diameter: 5 10 mm. Internode length: 2.5 to 3.5 cm. Stem color: 139C. Stem texture: Sparsely pubescent. Stem strength: Very strong. Stem base strength: Very strong.

*Foliage description.*—Leaf arrangement: Simple, alternate. Leaf length: 8 to 14 cm. Leaf width: About 10 cm. Leaf shape: Cordate. Leaf apex: Acute. Leaf base: Obtuse. Leaf margin: Serrate. Leaf texture: Upper surface: Smooth, leathery, glabrous. Lower surface: Leathery, sparsely pubescent. Leaf color: Young foliage, upper surface: 139A. Young foliage, lower surface: 139C. Mature foliage, upper surface: 139A. Mature foliage, lower surface: 138B. Petiole length: 1.5 to 6 cm. Petiole diameter: 3 to 5 mm. Petiole color: 139C. Venation pattern: Palmate, smooth on upper surface, prominent on lower surface. Venation color: Upper surface: 139C. Lower surface: 139D.

Flower descsription:

*Flowering habit.*—Flowers arranged in racemes. Many racemes in flower simultaneously. Flowering continuous under warm (higher than 18° C.) night temperatures.

*Time to flower.*—Under optimal environmental conditions, usually 4 to 6 weeks are required.

*Natural flowering season.*—Plants will flower year around regardless of daylength, however plants will flower earlier and more abundantly if daylength is 12 hours or less.

*Quantity of flowers.*—Six to 8 flowers per raceme, up to 60 flowers at various stages of development may be present per 15-cm pot.

*Flowers.*—Shape: Circular. Diameter: 2.5 to 4.5 cm. Height: About 1.5 cm. Aspect: Erect.

*Peduncle.*—Length: About 4 cm. Strength: Good. Color: 139C. Angle: About 45°.

*Flower bud.*—Shape Ovoid. Diameter: 5 mm. Length: 5 mm. Rate of opening: 3 to 5 days. Color: 26D.

*Petals.*—Arrangement: Rosette. Shape: Flat, rounded. Quantity per flower: 8 to 20. Length: 1.5 to 2 cm. Width: 1.5 to 2 cm. Apex: Rounded, obtuse. Color: When opening: Upper surface: 28A. Lower surface: 28D. Fully open: Upper surface: 28A. Lower surface: 28D. Margin: Entire. Texture: Smooth, velvety, glabrous.

*Sepals.*—Arrangement: Opposite. Shape: Rounded to oval, flat. Quantity per flower: 2. Color: Upper surface: 139C. Lower surface: 139C. Apex: Slightly pointed. Margin: Entire. Texture: Thin, transparent.

*Reproductive organs.*—Stamens: None. Pistils: None.

Postproduction longevity: Individual flowers generally maintain good condition for 2 to 3 weeks. Whole plants generally maintain good condition for about 6 weeks under interior conditions.

Disease resistance: Plants of the cultivar Betty are resistant to Powdery Mildew.

Seed production: Seed production has not been observed as reproductive organs are not formed.

I claim:

1. A new and distinct Elatior Begonia plant named Betty, as illustrated and described.

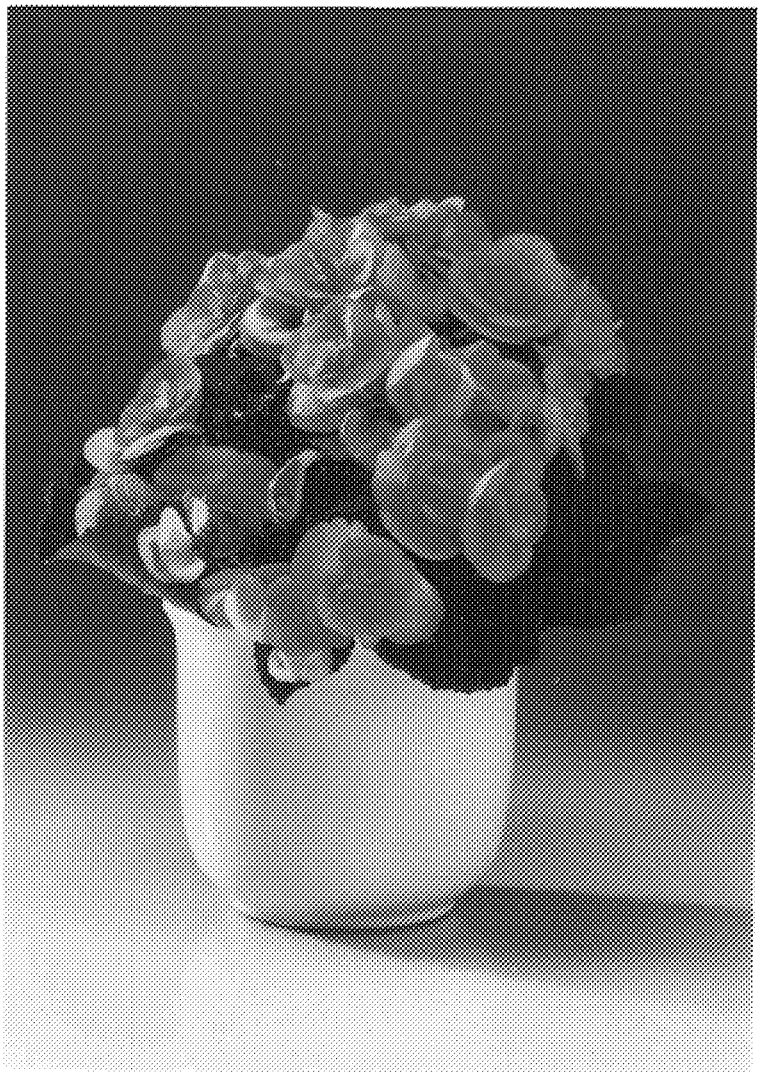

* * * * *